United States Patent
Li et al.

(10) Patent No.: US 8,744,128 B2
(45) Date of Patent: Jun. 3, 2014

(54) IMAGING SYSTEM AND IMAGE PROCESSING METHOD THEREOF

(75) Inventors: Arvin Huang-Te Li, Chiayi (TW); Yio-Wha Shau, Taipei (TW); Yu-Ching Chang, Hsinchu (TW); Bai-Kuang Hwang, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 111 days.

(21) Appl. No.: 13/558,362

(22) Filed: Jul. 26, 2012

(65) Prior Publication Data

US 2013/0163840 A1    Jun. 27, 2013

(30) Foreign Application Priority Data

Dec. 27, 2011   (TW) .............................. 100148936 A

(51) Int. Cl.
  *G06K 9/00*   (2006.01)
  *A61B 8/00*   (2006.01)

(52) U.S. Cl.
  USPC .......................... 382/103; 382/274; 600/443

(58) Field of Classification Search
  CPC ............ G06T 5/008; G06K 9/00; A61B 8/00
  USPC ........ 382/100, 103, 106–107, 128–133, 162, 382/168, 173, 181, 191, 219, 224, 232, 254, 382/274, 276, 286, 291, 305, 312; 378/16, 378/19; 600/443; 702/48
  See application file for complete search history.

(56) References Cited

U.S. PATENT DOCUMENTS

| | | | |
|---|---|---|---|
| 4,453,550 A | 6/1984 | Flax | |
| 5,919,139 A * | 7/1999 | Lin | 600/443 |
| 5,993,393 A | 11/1999 | Ryan et al. | |
| 6,023,968 A | 2/2000 | Spratt et al. | |
| 6,325,759 B1 * | 12/2001 | Pelissier | 600/443 |

(Continued)

FOREIGN PATENT DOCUMENTS

| | | |
|---|---|---|
| CN | 201223409 | 4/2009 |
| CN | 101904753 | 12/2010 |

(Continued)

OTHER PUBLICATIONS

Tsui et al, "Noise-Modulated Empirical Mode Decomposition," Advances in Adaptive Data Analysis 2 (1), 2010, pp. 25-37.

(Continued)

*Primary Examiner* — Seyed Azarian
(74) *Attorney, Agent, or Firm* — Jianq Chyun IP Office

(57) ABSTRACT

An image processing method is provided. The image processing method includes the following steps. A plurality of raw signal is received by a signal transceiving module of the ultrasound imaging system. It is determined whether each of the raw signals satisfies any condition in a condition group, and the raw signal satisfying any condition in the condition group is mapped to one of a plurality of preset constants to generate a plurality of first data. The raw signals not satisfying any condition in the condition group are processed according to a calculation formula to generate a plurality of second data. A beamforming procedure is simultaneously performed on the first and second data to obtain a beamformed image. The beamformed image is transformed to obtain an image of a region to be detected. Furthermore, an imaging system using the foregoing image processing method is also provided.

17 Claims, 3 Drawing Sheets

(56) References Cited

U.S. PATENT DOCUMENTS

| | | | |
|---|---|---|---|
| 6,937,776 B2 | 8/2005 | Li et al. | |
| 7,243,945 B2 | 7/2007 | Breed et al. | |
| 7,925,064 B2* | 4/2011 | Cloutier et al. | 382/128 |
| 7,984,651 B2 | 7/2011 | Randall et al. | |
| 2007/0288178 A1* | 12/2007 | Bonnefous | 702/48 |
| 2009/0247871 A1 | 10/2009 | Varghese et al. | |
| 2010/0010352 A1 | 1/2010 | Jong | |
| 2010/0081931 A1 | 4/2010 | Destrempes et al. | |
| 2010/0239144 A1 | 9/2010 | Fichtinger et al. | |
| 2010/0249671 A1 | 9/2010 | Coleman et al. | |
| 2010/0324423 A1 | 12/2010 | El-Aklouk et al. | |
| 2010/0329529 A1 | 12/2010 | Feldman et al. | |
| 2011/0054317 A1* | 3/2011 | Lin et al. | 600/443 |

FOREIGN PATENT DOCUMENTS

| | | |
|---|---|---|
| JP | 2008-515521 | 5/2008 |
| TW | 594032 | 6/2004 |
| TW | I252929 | 4/2006 |
| TW | 201012439 | 4/2010 |
| WO | 2005048190 | 5/2005 |

OTHER PUBLICATIONS

Tay et al, "Ultrasound Despeckling for Contrast Enhancement," IEEE Transactions on Image Processing 19(7), Jul. 2010, pp. 1847-1860.

Tsui et al., "An adaptive threshold filter for ultrasound signal rejection," Ultrasonics 49, 2009, pp. 413-418.

Nadernejad et al., "Despeckle Filtering in Medical Ultrasound Imaging," Contemporary Engineering Sciences 2 (1), 2009, pp. 17-36.

Phukpattaranont et al., "Optimum Quadratic Filters for Nonlinear Ultrasonic Imaging," Japanese Journal of Applied Physics 48, Jul. 21, 2009, pp. 07GJ02-1-07GJ02-7.

Dantas et al., "Ultrasound Speckle Reduction Using Modified Gabor Filters," IEEE Transactions on Ultrasonics, Ferroelectrics and Frequency Control 54(3), Mar. 2007, pp. 530-538.

Michailovich et al., "Despeckling of Medical Ultrasound Images," IEEE Transactions on Ultrasonics, Ferroelectrics and Frequency Control 53(1), Jan. 2006, pp. 64-78.

Kim et al., "Improvement of Ultrasound Image Based on Wavelet Transform: Speckle Reduction and Edge Enhancement," Medical Imaging 2005: Image Processing (Proc. of SPIE) 5747, 2005, pp. 1085-1092.

Mu et al., "Iterative Ultrasonic Signal and Image Deconvolution for Estimation of the Complex Medium Response," IEEE Transactions on Ultrasonics, Ferroelectrics and Frequency Control 15(6), 2005, pp. 266-277.

Kozumplík, "Wavelet Packet Transform in Raw Ultrasound Signal Processing," Journal of Electrical Engineering 54(1-2), 2003, pp. 42-46.

Abd-Elmoniem et al., "Real-Time Speckle Reduction and Coherence Enhancement in Ultrasound Imaging via Nonlinear Anisotropic Diffusion," IEEE Transactions on Biomedical Engineering 49(9), Sep. 2002, pp. 997-1014.

"Office Action of Taiwan Counterpart Application", issued on Apr. 3, 2014, p. 1-p. 4.

\* cited by examiner

| Raw signal S1 satisfying the condition group | Generated first data S1' |
|---|---|
| $-e < S1 < -1$ | S1 |
| $S1 = -1$ | $-1$ |
| $-1 < S1 < 0$ | 0 |
| $S1 = 0$ | 0 |
| $0 < S1 < 1$ | 0 |
| $S1 = 1$ | 1 |
| $1 < S1 < e$ | $-S1$ |
| $S1 = e$ | $-S1$ |

FIG. 2

IMAGING SYSTEM AND IMAGE PROCESSING METHOD THEREOF

CROSS-REFERENCE TO RELATED APPLICATION

This application claims the priority benefit of Taiwan application serial no. 100148936, filed on Dec. 27, 2011. The entirety of the above-mentioned patent application is hereby incorporated by reference herein and made a part of this specification.

TECHNICAL FIELD

The technical field relates to an imaging system and an image processing method thereof.

BACKGROUND

Generally, an ultrasound imaging system includes a probe, and the probe is connected to a data processing module and an image display module of the ultrasound imaging system through transmission lines. The probe generally includes an ultrasound transducer array. In a medical ultrasound inspection, the probe produces sound waves through short and strong sound pulses produced by the phased array of the transducers, and transmits the ultrasound energy to a region to be detected. Then, the transducers receive ultrasound energy reflected by the region.

The transducers transform the received ultrasound energy into voltage signals for transmitting to the data processing module. The data processing module processes the signals transmitted from the transducers by using a beamforming technique, so as to produce an ultrasound inspection image of the region to be detected.

However, in the medical ultrasound inspection, the contrast of ultrasound images is very important in interpretation of an inspection result. When conventional ultrasound imaging system is used for inspection, the obtained inspection image is not ideal. Therefore, it is necessary to provide a better ultrasound imaging system and an image processing method thereof to obtain ultrasound inspection images with a clear contrast.

SUMMARY

An embodiment of the disclosure provides an image processing method, which is adapted to an ultrasound imaging system. The image processing method includes the following steps: (a) a plurality of raw signals is received; (b) it is determined whether each of the raw signals satisfies any condition in a condition group, and the raw signal satisfying said condition is mapped to one of a plurality of predetermined constants to generate a plurality of first data after a first iteration; (c) the raw signals not satisfying any condition in the condition group are processed according to a calculation formula to generate a plurality of second data after the first iteration; (d) a beamforming procedure is simultaneously performed on the first and second data to obtain a beamformed image; (e) the beamformed image is transformed to obtain a processed image.

Another embodiment of the disclosure provides an ultrasound imaging system including a signal transceiving module, a signal processing module and an image display module. The signal transceiving module receives a plurality of raw signals. The signal processing module determines whether each of the raw signals satisfies any condition in a condition group, and maps each of the raw signals satisfying said condition to one of a plurality of predetermined constants to generate a plurality of first data after a first iteration. The signal processing module processing the raw signals not satisfying any condition in the condition group according to a calculation formula to generate a plurality of second data after the first iteration. The signal processing module simultaneously performs a beamforming procedure on the first and the second data to obtain a beamformed image. The signal processing module transforms the beamformed image to obtain a processed image. The image display module displays the processed image according to a transformed result of the beamformed image.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included for better understanding of the disclosure, and are incorporated in and constitute a part of this specification. The drawings illustrate embodiments of the disclosure and, together with the description, serve to explain the principles of the disclosure.

FIG. 2 illustrates a mapping relationship of raw signals satisfying a condition group and first data according to an embodiment of the disclosure.

DETAILED DESCRIPTION

Figure 1:
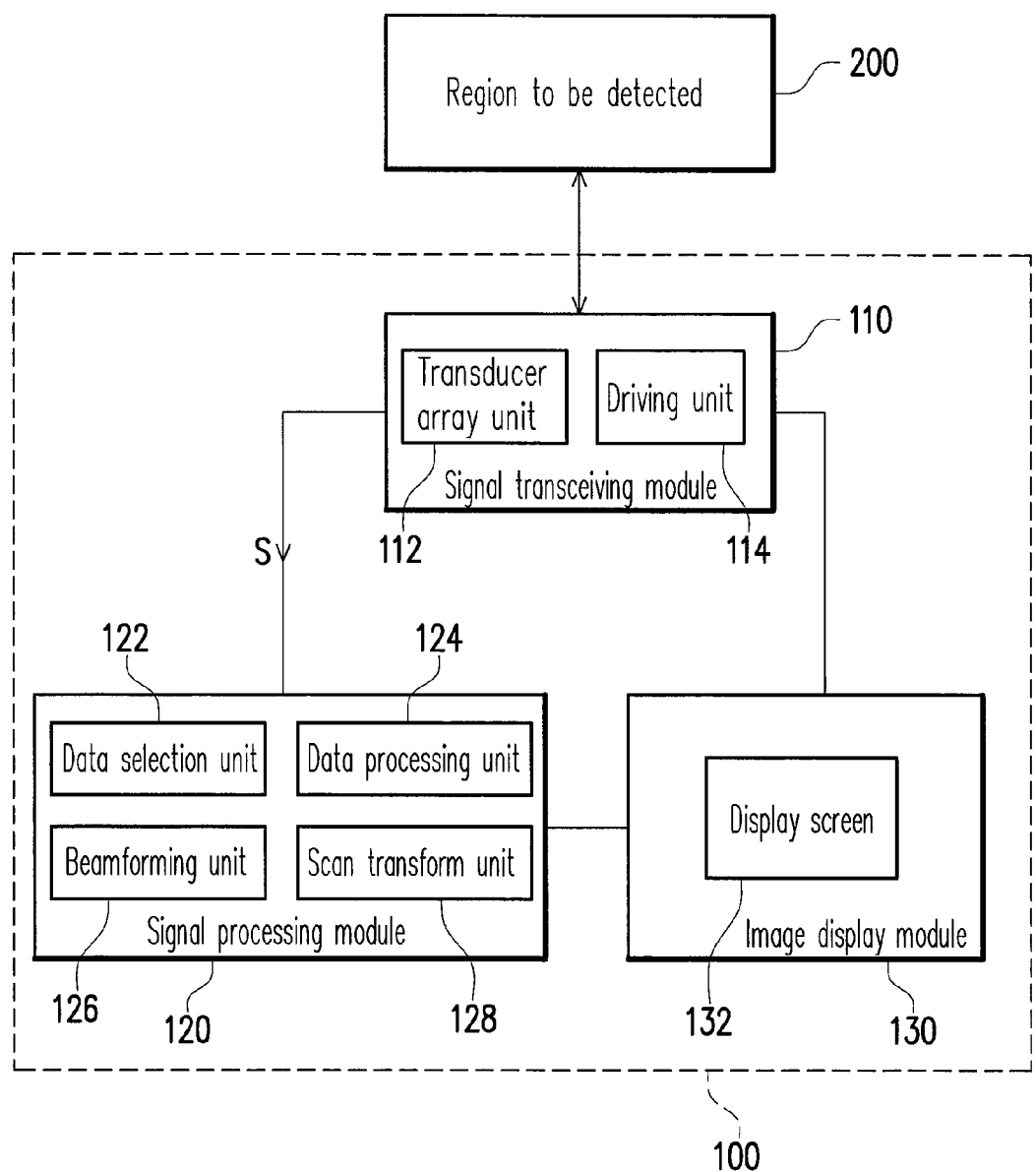
FIG. 1 is a block schematic diagram of an ultrasound imaging system according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

An image processing method provided by an exemplary embodiment of the disclosure is adapted to ultrasound imaging systems of different design structures. According to the method, after a front-end ultrasound probe transmits and receives raw signals, a preset selective condition group and a calculation formula is used to filter and process the raw signals. Moreover, regarding processing of the raw signals, the method can perform an iterative process once or multiple times according to an actual design requirement, so as to improve an image contrast. After the raw signals are processed by the aforementioned procedure, a "beamforming" procedure is performed at a back-end for imaging, so as to obtain an image with a clearer contrast compared to that obtained according to a conventional method by which the front-end processing is not performed. In order to fully convey the spirit of the disclosure, at least one exemplary embodiment is provided below for descriptions with reference to figures.

FIG. 1 is a block schematic diagram of an ultrasound imaging system according to an embodiment of the disclosure. Referring to FIG. 1, the ultrasound imaging system 100 of the present embodiment includes a signal transceiving module 110, a signal processing module 120 and an image display module 130. The signal transceiving module 110 includes a transducer array unit 112 and a driving unit 114. In the present embodiment, the driving unit 114 provides a driving signal to transducers in the transducer array unit 112 to trigger each of the transducers to transmit an ultrasound signal to a region 200 to be detected. The transducer array unit 112 generates ultrasound signals after being triggered, and transmits the ultrasound signals to the region 200 to be detected (for example, a human tissue or other transmission media). Then, an ultrasound reflected wave reflected by the region 200 to be detected is again received by the transducer array unit 112, and the signal processing module 120 obtains raw signals S from the region to be detected. In the present embodiment, an image of the region to be detected is, for example, a B-mode image of a conventional ultrasound system, and the raw signal refers to a signal that is not yet processed by beamforming procedure.

In the present embodiment, after the transducer array unit 112 receives the wave reflected by the region 200 to be detected, the transducer array unit 112 may convert the reflected analog wave signals to digital signals. In other words, the transducer array unit 112 may further include an analog-to-digital converter, which is used for converting the reflected analog wave signals to digital signals, though the disclosure is not limited thereto. In other embodiments, the analog-to-digital conversion function can also be implemented by a circuit in internal of the driving unit 114, or implemented by an interface circuit between the signal transceiving module 110 and the signal processing module 120, which is not limited by the disclosure.

After receiving the raw signals S from the region 200 to be detected, the signal processing module 120 of the present embodiment first filters the raw signal, and then performs the iterative process once or multiple times according to an actual design requirement.

In detail, the signal processing module 120 of the present embodiment includes a data selection unit 122, a data processing unit 124, a beamforming unit 126 and a scan transform unit 128. The data selection unit 122 determines whether each raw signal satisfies any condition in a condition group, and maps the raw signal satisfying said condition in the condition group to one of a plurality of predetermined constants to generate a plurality of first data after a first iteration. Here, the condition group can be preset in the data selection unit 122 according to an actual design requirement. In the following exemplary embodiments, the raw signals S that satisfy said condition is represented by raw signal S1, and the raw signals S that do not satisfy any condition in the condition group is represented by raw signal S2. Namely, a combination of the raw signals Si satisfying any conditions in the condition group and the raw signals S2 not satisfying any conditions in the condition group is equal to the raw signals S received by the data selection unit 122.

FIG. 2 illustrates a mapping relationship of the raw signal satisfying any condition in the condition group and the first data. Referring to FIG. 1 and FIG. 2, the condition group of the present embodiment includes a plurality of predetermined values and a plurality of predetermined ranges as that shown in FIG. 2, though the disclosure is not limited thereto. The predetermined values of the condition group include −1, 0, 1 and e, where e is the base of natural logarithm with a numerical value approximately equal to 2.71828182845905. The data selection unit 122 determines whether the received raw signal S is equal to one of the predetermined value −1, 0, 1 and e. If it is determined that the raw signal S is equal to one of the predetermined value −1, 0, 1 and e, the data selection unit 122 maps the raw signals S1 equalling to said predetermined value to the predetermined constants to generate first data S1' corresponding to each of the raw signals. For example, in FIG. 2, S1 represents the raw signal equalling to said predetermined value, and S1' represents the first data generated by mapping to the predetermined constants. When the raw signal S1 related to the region 200 to be detected is equal to the predetermined value −1, the data selection unit 122 maps the raw signal S1=−1 to the predetermined constant S1'=−1, that is, S1=−1 and S1'=−1. Similarly, when the raw signal S1 is equal to the predetermined value 0 or 1, the data selection unit 122 maps the raw signal 0 or 1 to the predetermined constant 0 or 1, i.e. S1=0 and S1'=0; S1=1 and S1'=1. Moreover, when the raw signal S1 is equal to the predetermined value e, the data selection unit 122 maps the raw signal e to the predetermined constant −S1, that is, S1=e and S1'=−S1.

On the other hand, the predetermined ranges of the condition group of the present embodiment include −e<S1<−1, −1<S1<0, 0<S1<1 and 1<S1<e. The data selection unit 122 also determines whether the received raw signal S1 falls in any of the predetermined ranges. If it is determined that the received raw signal S1 falls in one of the predetermined ranges, the data selection unit 122 maps the raw signals S1 falling in any of the predetermined ranges to the predetermined constants to generate the first data S1' corresponding to each of the raw signals. For example, when the raw signal S1 from the region 200 to be detected falls in the predetermined range 0<S1<1, the data selection unit 122 maps the raw signal S1 to the predetermined constant S1'=0, that is, 0<S1<1 and S1'=0. Similarly, when the raw signal S1 falls in the predetermined range −1<S1<0, the data selection unit 122 maps the raw signal S1 to the predetermined constant 0, that is, −1<S1<0, and S1'=0. Moreover, when the raw signal S1 falls in the predetermined range −e<S1<−1, the data selection unit 122 maps the raw signal S1 to the predetermined constant −S1, that is, −e<S1<−1, and S1'=−S1. When the raw signal S1 falls in the predetermined range 1<S1<e, the data selection unit 122 maps the raw signal S1 to the predetermined constant −S1, that is, 1<S1<e, and S1'=−S1. Therefore, by using the condition group to filter the raw signals, additional noises can be reduced to enhance the original reflected wave signal.

After the data selection unit 122 preliminarily filters the raw signals S by using the predetermined values and the predetermined ranges of the aforementioned condition group, the data processing unit 124 processes the raw signals S2 not satisfying any conditions in the condition group according to a calculation formula, so as to generate a plurality of second data S2' after the first iteration. Moreover, since the raw signals S of the present embodiment have been preliminarily filtered according to the aforementioned condition group, the processing time of the data processing unit 124 is reduced.

In detail, the calculation formula of the present embodiment is as follows:

$$S2'=S2\times(ln|S2|)-S2$$

Where S2' is the second data, S2 is the raw signal not satisfying the condition group, and ln|S2| is a logarithmic function value of an absolute value of S2. In other words, the calculation formula of the present embodiment includes a specific function value ln|S2| of each of the raw signals S2 and four basic arithmetic operations of the raw signal S2. Here, the specific function is, for example, a logarithmic function, and the four basic arithmetic operations include multiplication and subtraction.

In the present embodiment, according to the condition group shown in FIG. 2, if the raw signal S2<−e or S2>e, it is the raw signal not satisfying the condition group, and the data processing unit 124 processes the raw signal S2<−e or S2>e according to the aforementioned calculation formula to obtain the corresponding second data. For example, if the raw signal S2 is 3, it does not satisfies the preset condition group, and the data processing unit 124 feeds the raw signal S2=3 to the aforementioned calculation formula to obtain the second data after the first iteration. After the first iteration, when the first and the second data are obtained, the data selection unit 122 and the data processing unit 124 can repeatedly perform the aforementioned data filtering and processing steps to obtain the first and second data after multiple iterations.

Then, after the first and second data after the first or multiple iterations are obtained, the beamforming unit 126 performs beamforming and focusing procedure on said first and second data. As described above, the transducers in the transducer array unit 112 receive the waves reflected by the region 200 to be detected. Regarding each of the transducers, a delay time thereof is different, so that a beamforming circuit is required to separately delay the raw signal of each of the reflected waves. Therefore, the beamforming unit 126 includes a beamforming circuit to suitably introduce a differential delay to each of the received raw signal, so as to dynamically focus the signal to produce an accurate image of the region to be detected (or referred to as a beamformed image).

Then, the scan transform unit 128 converts the beamformed image produced by the beamforming unit 126 from polar coordinates to rectangular coordinates. Then, the scan transform unit 128 converts the format of the beamformed image and facilitates the image display module 130 to display the transformed image on a display screen 132. Compared to the conventional image, after the back-end imaging processing (that is, the processed image) of the raw signals processed by the image processing method of the present embodiment, the image contrast of the ultrasound imaging system is improved.

Figure 3:
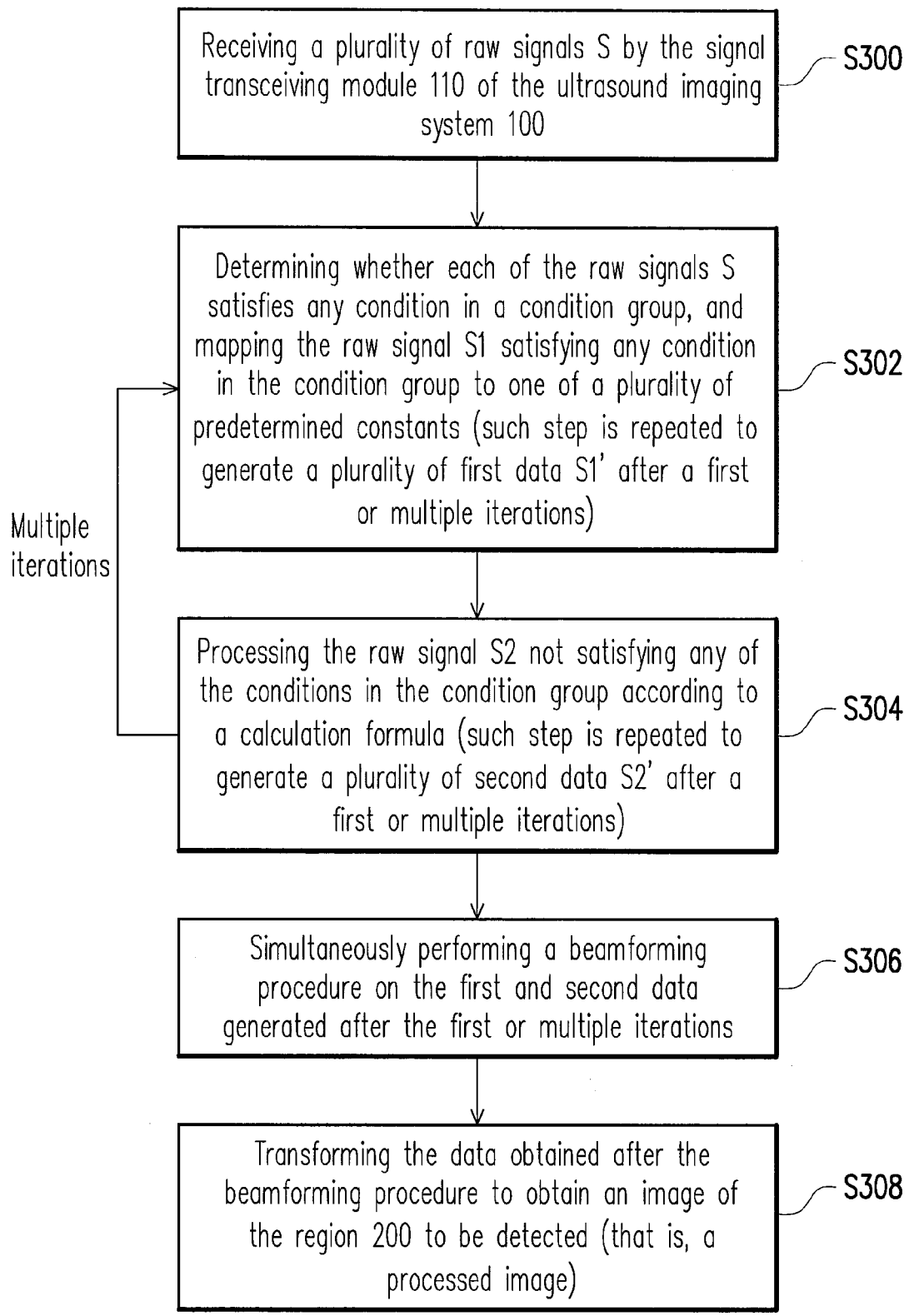
FIG. 3 is a flowchart illustrating an image processing method according to an embodiment of the disclosure.

FIG. 3 is a flowchart illustrating an image processing method according to an embodiment of the disclosure. Referring to FIG. 1 and FIG. 3, the image processing method of the present embodiment is adapted to the ultrasound imaging system shown in FIG. 1, and includes following steps. First, in step S300, the signal transceiving module 110 of the ultrasound imaging system 100 is used to receive a plurality of raw signals S. Then, in step S302, it is determined whether each of the raw signals S satisfies any condition in a condition group as that shown in FIG. 2, and the raw signal S1 satisfying said condition is mapped to one of a plurality of predetermined constants, and such step is repeated to generate a plurality of first data S1' after a first or multiple iterations. Then, in step S304, the raw signal S2 not satisfying any of the conditions in the condition group is processed according to a calculation formula, and such step is repeated to generate a plurality of second data S2' after a first or multiple iterations. Then, in step S306, a beamforming procedure is simultaneously performed on the first and second data generated after the first or multiple iterations. Then, in step S308, the data obtained after the beamforming procedure is transformed to obtain an image of the region 200 to be detected (that is, a processed image).

It should be noticed that the first or multiple iterative processes can be performed in allusion to the raw signal processing according to an actual design requirement, so as to improve an image contrast. Therefore, after the step S304, the step S302 can be returned to again perform the data filtering and operation on the first and second data obtained after the first iteration. Now, in the step S306, the processed data are the first and second data generated after multiple iterations. On the other hand, the image processing method of the present embodiment can be implemented by software or a field programmable gate array (FPGA) chip or other software or hardware approaches, which is not limited by the disclosure.

Moreover, since those skilled in the art can learn enough instructions and recommendations of the image processing method of the disclosure from the descriptions of the embodiments of FIG. 1 and FIG. 2, detailed description thereof is not repeated In summary, according to the exemplary embodiment of the disclosure, in the image processing method, after the front-end obtains the raw signals, it filters and computes the raw signals according to the predetermined selective condition group and the calculation formula, and performs a first or multiple iterative processes according to an actual design requirement, so as to improve the image contrast.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An image processing method, adapted to an ultrasound imaging system, and the image processing method comprising:
   (a) receiving a plurality of raw signals;
   (b) determining whether each of the raw signals satisfies any condition in a condition group, and mapping the raw signals satisfying said condition to one of a plurality of predetermined constants to generate a plurality of first data after a first iteration;
   (c) processing the raw signals not satisfying any condition in the condition group according to a calculation formula to generate a plurality of second data after the first iteration;
   (d) simultaneously performing a beamforming procedure on the first and second data to obtain a beamformed image;
   (e) transforming the beamformed image to obtain a processed image;
   further comprising:
   repeating the step (b) and the step (c) in allusion to the generated first and second data to obtain the first and the second data generated after multiple iterations.

2. The image processing method as claimed in claim 1, wherein in the step (d), the beamforming procedure is simultaneously performed on the first and second data generated after the first or multiple iterations.

3. The image processing method as claimed in claim 1, wherein in the step (b), the condition group comprises a plurality of predetermined values, and when the raw signal equals any of the predetermined values, each of the raw signals equalling to said predetermined value is mapped to one of the predetermined constants to generate the first data.

4. The image processing method as claimed in claim 3, wherein situations of mapping each of the raw signals equalling to any of the predetermined values to one of the predetermined constants when the raw signal equals to any of the predetermined values comprise:
   if S1=−1, mapping S1 to −1 to generate S1'=1;
   if S1=0, mapping S1 to 0 to generate S1'=0;
   if S1=1, mapping S1 to 1 generate S1'=1; and
   if S1=e, mapping S1 to −S1 to generate S1'=−S1,
   wherein S1 is the raw signal equalling to any of the predetermined values −1, 0, 1 and e, S1' is the first data, and e is the base of natural logarithm.

5. The image processing method as claimed in claim 4, wherein situations of mapping each of the raw signals falling in any of the predetermined ranges to one of the predetermined constants when said raw signal falls in said predetermined ranges comprise:
if $-e<S1<-1$, mapping S1 to S1 to generate S1'=S1;
if $-1<S1<0$, mapping S1 to 0 to generate S1'=0;
if $0<S1<1$, mapping S1 to 0 to generate S1'=0; and
if $1<S1<e$, mapping S1 to $-S1$ to generate S1'=S1,
wherein S1 is the raw signal falling in one of the predetermined ranges, S1' is the first data, and e is the base of natural logarithm.

6. The image processing method as claimed in claim 1, wherein in the step (b), the condition group comprises a plurality of predetermined ranges, and when the raw signals fall in one of the predetermined ranges, each of the raw signals falling in one of the predetermined ranges is mapped to one of the predetermined constants.

7. The image processing method as claimed in claim 1, wherein in the step (c), the calculation formula comprises a specific function of the raw signal and operations of the raw signal itself.

8. The image processing method as claimed in claim 7, wherein in the step (c), the calculation formula is as follows:

$$S2'=S2*(ln|S2|)-S2$$

wherein S2' is the second data, S2 is the raw signal not satisfying any condition in the condition group, and ln|S2| is a logarithmic function value of an absolute value of S2.

9. An ultrasound imaging system, comprising:
a signal transceiving module, receiving a plurality of raw signals;
a signal processing module, determining whether each of the raw signals satisfies any condition in a condition group, and mapping the raw signals satisfying said condition to one of a plurality of predetermined constants to generate a plurality of first data after a first iteration; processing the raw signals not satisfying any condition in the condition group according to a calculation formula to generate a plurality of second data after the first iteration; simultaneously performing a beamforming procedure on the first and second data to obtain a beamformed image; and transforming the beamformed image to obtain a processed image; and
an image display module, displaying the processed image according to a transformed result of the beamformed image;
wherein the signal processing module repeatedly determining whether the generated first and the second data satisfy any condition in the condition group, and repeatedly performing the process on the first and second data not satisfying any condition in the condition group, so as to obtain the first and the second data generated after multiple iterations.

10. The ultrasound imaging system as claimed in claim 9, wherein the signal processing module comprises:
a data selection unit, determining whether each of the raw signals satisfies any condition in the condition group, and mapping the raw signals satisfying said condition to one of a plurality of predetermined constants to generate a plurality of the first data after a first iteration;
a data processing unit, processing the raw signals not satisfying any condition in the condition group according to the calculation formula to generate a plurality of the second data after the first iteration;
a beamforming unit, simultaneously performing the beamforming procedure on the first and second data to obtain the beamformed image; and
a scan transform unit, transforming the beamformed image to obtain the processed image.

11. The ultrasound imaging system as claimed in claim 9, wherein the signal processing module simultaneously performs the beamforming procedure on the first and second data generated after the first or multiple iterations.

12. The ultrasound imaging system as claimed in claim 9, wherein the condition group comprises a plurality of predetermined values, and when the raw signal equals to any of the predetermined values, the signal processing module maps each of the raw signals equalling to said predetermined values to one of the predetermined constants.

13. The ultrasound imaging system as claimed in claim 12, wherein situations of mapping each of the raw signals equalling to any of the predetermined values to one of the predetermined constants when the raw signal equals to any of the predetermined values comprise:
if S1=$-1$, mapping S1 to $-1$ to generate S1'=$-1$;
if S1=0, mapping S1 to 0 to generate S1'=0;
if S1=1mapping S1 to 1 to generate S1'=1; and
if S1=e, mapping S1 to $-S1$ to generate S1'=$-S1$,
wherein S1 is the raw signal equalling to any of the predetermined values $-1$, 0, 1 and e, S1' is the first data, and e is the base of natural logarithm.

14. The ultrasound imaging system as claimed in claim 12, wherein the calculation formula is as follows:

$$S2'=S2*(ln|S2|)-S2$$

wherein S2' is the second data, S2 is the raw signal not satisfying any condition in the condition group, and ln|S2| is a logarithmic function value of an absolute value of S2.

15. The ultrasound imaging system as claimed in claim 9, wherein the condition group comprises a plurality of predetermined ranges, and when the raw signal falls in any of the predetermined ranges, the signal processing module maps said raw signals falling in said predetermined ranges to one of the predetermined constants.

16. The ultrasound imaging system as claimed in claim 15, wherein situations of mapping each of the raw signals falling in any of the predetermined ranges to one of the predetermined constants when said raw signal falls in said predetermined ranges comprise:
if $-e<S1<31\ 1$, mapping S1 to S1 to generate S1'=S1;
if $-1<S1<0$, mapping S1 to 0 to generate S1'=0;
if $0<S1<1$, mapping S1 to 0 to generate S1'=0; and
if $1<S1<e$, mapping S1 to $-S1$ to generate S1'=$-S1$,
wherein S1 is the raw signal falling in any of the predetermined ranges, S1' is the first data, and e is the base of natural logarithm.

17. The ultrasound imaging system as claimed in claim 9, wherein the calculation formula comprises a specific function of the raw signals and operations of the raw signal itself.

* * * * *